United States Patent [19]

Ninomiya et al.

[11] Patent Number: 5,112,532
[45] Date of Patent: May 12, 1992

[54] NON-LINEAR OPTICAL MATERIAL AND NON-LINEAR OPTICAL DEVICE EMPLOYING IT

[75] Inventors: Hidetaka Ninomiya; Noritaka Nakayama; Toyoaki Masukawa; Miki Morita, all of Tokyo, Japan

[73] Assignee: Konica Corporation, Tokyo, Japan

[21] Appl. No.: 384,965

[22] Filed: Jul. 24, 1989

[30] Foreign Application Priority Data

Jul. 30, 1988 [JP] Japan ................. 63-191021

[51] Int. Cl.$^5$ ............ F21V 9/04; F21V 9/00; G02B 6/10
[52] U.S. Cl. .................. 252/587; 252/582; 252/589; 359/322; 359/328; 359/332
[58] Field of Search ........ 252/587, 589, 582; 350/96.12, 96.13, 96.14, 96.23, 96.29, 96.3, 96.31, 96.32, 96.33, 96.34; 359/326, 328, 332, 322

[56] References Cited

U.S. PATENT DOCUMENTS

| | | | |
|---|---|---|---|
| 4,830,447 | 5/1989 | Kamiyama et al. | 350/96.12 |
| 4,876,688 | 10/1989 | Wang et al. | 372/22 |
| 4,981,613 | 1/1991 | Okazaki et al. | 252/587 |
| 4,982,112 | 1/1991 | Okazaki et al. | 307/425 |
| 4,994,209 | 2/1991 | Okazaki et al. | 252/587 |
| 5,016,958 | 5/1991 | Booth | 350/96.13 |

FOREIGN PATENT DOCUMENTS

3707835 9/1987 Fed. Rep. of Germany ...... 252/587

OTHER PUBLICATIONS

Twieg, R. et al, Energy Res. Abstr. 1986, 11(7) Abstr No 14993.
Tokutake, S. et al Mol. Cryst. Liq. Cryst. 170, 245, 1989.
Chemical Abstracts, vol. 111, No. 20, Nov. 13, 1989, p. 653, col. 2 Abstract No. 183,896z; JPA-1-50,032; Feb. 27, 1989.
Chemical Abstracts, vol. 111, No. 10, Sep. 4, 1989, p. 615, col. 1, Abstract No. 87,080h; JPA-1-52,131; Feb. 28, 1989.
Chemical Abstracts, vol. 111, No. 10, Sep. 4, 1989, p. 615, col. 2, Abstract No. 87,085q; JPA-1-66,625; Mar. 13, 1989.
Chemical Abstracts, vol. 111, No. 10, Sep. 4, 1989, p. 614, col. 2, Abstract No. 87,078p; JPA-1-40-463; Feb. 10, 1989.

Primary Examiner—Robert L. Stoll
Assistant Examiner—Philip Tucker
Attorney, Agent, or Firm—Jordan B. Bierman

[57] ABSTRACT

A novel organic non-linear optical material and a device using the same are disclosed. The material hardly makes reversal symmetrical molecular configuration in a bulk state such as a crystal and a thin layer and shows a high non-linear optical effect. A non-linear optical device using the material has an excellent properties. The organic non-linear optical material is comprised of the following compound:

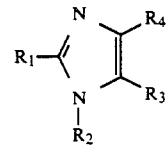

wherein $R_1$, $R_3$ and $R_4$ are independently a hydrogen atom, a cyano group, a phenyl group, an amino group, an alkoxy group, an acylamino group, an alkylthio group, an alkyl group, an alkoxycarbonyl group, carbamoyl group or a heterocyclic group, provided that $R_3$ is allowed to link together with $R_4$ to form a ring and $R_1$, $R_3$ and $R_4$ are not hydrogen atom at the same time; $R_2$ is a hydrogen atom, an alkyl group or an acyl group; and said groups represented by $R_1$, $R_2$, $R_3$, $R_4$ and the ring formed by linking the groups represented by $R_3$ and $R_4$ are allowed to have a substituent.

4 Claims, No Drawings

NON-LINEAR OPTICAL MATERIAL AND NON-LINEAR OPTICAL DEVICE EMPLOYING IT

FIELD OF THE INVENTION

This invention relates to an organic non-linear optical material applicable to the generation of the higher harmonic waves and to the parametric amplification of laser beam, and to the like, and further relates to an organic non-linear optical device, employing it.

BACKGROUND OF THE INVENTION

A non-linear optical effect is strikingly displayed when exposing a material to intensive light such as laser beams. Such effect can be applied to a frequency conversion, an intensity moderation, a switching operation, and so forth. In recent years, many researches and developments have been made for obtaining the materials capable of displaying such a non-linear optical effect so far. Regarding such research and development of the non-linear optical material, "Non-linear Optical Properties of Organic Molecules and Crystals, vol. 1, 2, edited by AT&T, Academic Press Inc. '87", can be referred.

For the frequency conversion and, in particular, for the Second Harmonic Generation (hereinafter abbreviated to SHG) originated from the second-order non-linear optical effect, there have been some indications of the possibility that an organic compound may display extraordinarily higher efficiency than those of the conventionally known inorganic materials such as lithium niobate ($LiNbO_3$), potassium dihydrogenphosphate (KDP), and so forth. Such an indication is found out in, for example, "Organic Non-linear Optical Materials", compiled under the supervision of Masao Kato and Hachiro Nakanishi, published by C.M.C. Company, Japan, 1985.

The optical non-linearity of an organic compound originates from $\pi$ electrons of molecules, and the second-order non-linear molecular polarizability ($\beta$) becomes particularly greater when the above-mentioned compound has both an electron donative group and an electron attractive group.

There are, however, many compounds including, typically, p-nitroaniline which display no SHG at all or a few in their crystalline arrangement, even if they have a great molecular non-linear polarizability. This is because the molecular orientation in the crystals of polar organic compounds are liable to be centrosymmetric in crystalline arrangement.

SUMMARY OF THE INVENTION

It is, accordingly, an object of the invention to provide a novel organic non-linear optical material which can hardly be inversely symmetric in a bulk state such as those of crystals, thin films and so forth, and is capable of displaying a high non-linear optical effect and, further, an organic non-linear optical device employing the material.

The above-mentioned object of the invention can be achieved with a non-linear optical material comprised of a compound represented by the following Formula I and a non-linear optical device employed the above-mentioned material.

Formula I

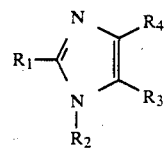

wherein $R_1$, $R_3$ and $R_4$ independently a hydrogen atom, a cyano group, a phenyl group, an amino group, an alkoxy group, acylamino group, an alkylthio group, an alkyl group, an alkoxycarbonyl group, a carbamoyl group, or a heterocyclic group, provided that $R_3$ is allowed to link together with $R_4$ to form a ring and $R_1$, $R_3$ and $R_4$ shall not be hydrogen atoms at the same time; $R_2$ is a hydrogen atom, an alkyl group or an acyl group, and the groups represented by $R_1$, $R_2$, $R_3$, $R_4$ and the ring formed by linking the groups represented by $R_3$ and $R_4$ are allowed to have a substituent.

DETAILED DESCRIPTION OF THE INVENTION

The invention will now be more detailed below.

In the above-given Formula I, amino groups represented by $R_1$, $R_3$ and $R_4$ include, for example, a methylamino group, a dimethylamino group and so forth.

Alkoxy groups represented by $R_1$, $R_3$ and $R_4$ include, for example, a methoxy group, an ethoxy group, and so forth.

Acylamino groups represented by $R_1$, $R_3$ and $R_4$ include, for example, a benzamido group, an acetoamido group, and so forth.

Alkylthio groups represented by $R_1$, $R_3$ and $R_4$ include, for example, a methylthio group, and so forth.

Alkyl groups represented by $R_1$, $R_3$ and $R_4$ include, for example, a methyl group, an ethyl group, and so forth.

Alkoxycarbonyl groups represented by $R_1$, $R_3$ and $R_4$ include, for example, a methyl carboxylate group, and so forth.

Carbamoyl groups represented by $R_1$, $R_3$ and $R_4$ include, for example, a methyl carbamoyl group, a phenylcarbamoyl group, and so forth.

Heterocyclic groups represented by $R_1$, $R_3$ and $R_4$ include, for example, a pyridyl group, a pyrazolyl group, an imidazolyl group, a pyrimidyl group, a furyl group, a thienyl group, and so forth.

The preferable groups represented by $R_1$, $R_3$ and $R_4$ include, for example, a substituted phenyl group.

The preferable rings completed by linking $R_3$ and $R_4$ together include, for example, a benzene ring.

The rings completed by linking $R_3$ and $R_4$ together are allowed to have a substituent.

Alkyl groups represented by $R_2$ include, for example, a methyl group, an ethyl group, and so forth.

Acyl groups represented by $R_2$ include, for example, a benzoyl group, an acetyl group, and so forth.

The preferable ones represented by $R_2$ include, for example, a hydrogen atom.

$R_1$, $R_2$, $R_3$ and $R_4$ are each allowed to have a substituent.

There is no special limitation to the substituents, but they may be selected from the following electron attractive or electron donative substituents.

The above-mentioned electron attractive substituents are those having a Hammett's constant $\sigma p$ more than zero. They include, for example, nitro groups, cyano groups, alkylsulfonyl groups such as a methylsulfonyl group, a ethylsulfonyl group and so forth, formyl groups, carbamoyl groups such as a methyl carbamoyl group, a phenylcarbamoyl group, and so forth, sulfamoyl groups such as a methylsulfamoyl group, and so forth, oxycarbonyl groups such as a methoxycarbonyl group, an ethoxycarbonyl group, and so forth, dicyanovinyl groups, carboxy groups, and so forth.

Among these, a nitro group, a cyano group, an alkylsulfonyl group, a formyl group and an alkoxycarbonyl group are preferable.

The above-mentioned electron donative substituents are a halogen atom or those having a Hammett's constant $\sigma p$ less than zero. They include, for example, amino groups such as an amino group, a methylamino group, a dimethylamino group, a L-2-hydroxymethyl-1-pyrrolidinyl group, and so forth, hydroxyl groups, alkoxy groups such as a methoxy group, an ethoxy group, a butoxy group, and so forth, alkyl groups such as a methyl group, an ethyl group, a propyl group, and so forth.

The compounds represented by Formula I preferably include, for example, those having $R_1$ representing a phenyl group substituted with an electron attractive substituent and $R_4$ representing a phenyl group substituted with an electron donative substituent, or those having $R_1$ representing a phenyl group substituted with an electron donative substituent and $R_4$ representing a phenyl group substituted with an electron attractive substituent.

The compounds preferably applicable to the invention will be exemplified below. It is, however, to be understood that the invention shall not be limited thereto.

-continued

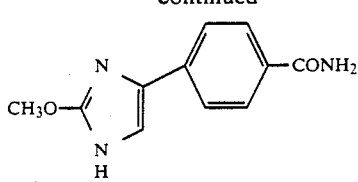
14

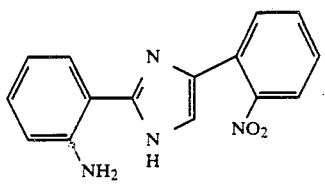
15

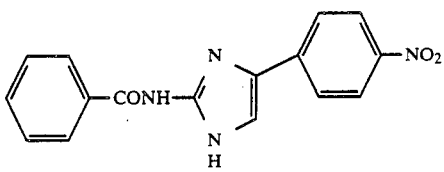
16

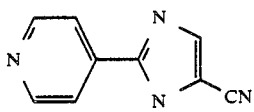
17

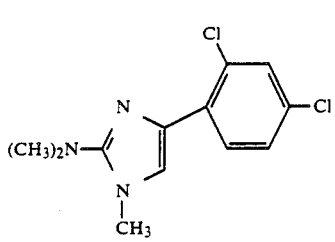
18

The imidazole rings of the compounds relating to the invention may usually be synthesized by making use of amidine having RI and bromacetophenone having $R_3$ and $R_4$. For further details, refer to Chemische Berichte, 34, 637 and, idem, 29, 2097, for example.

The other known synthesizing methods are described in, for example, Chemische Berichte, 38, 1531, id. 35, 2630, Annalen der Chemie, 600, 95–108, id. 663, Synthesis, 1978, 6, Journal of Chemical Society, 1957, 4225, and so forth.

The benzimidazole rings of the compounds relating to the invention are usually synthesized through a dehydration reaction of an o-phenylenediamine derivative with a carboxylic acid derivative.

When $R_2$ represents an alkyl group or an acyl group, the imidazole rings may be synthesized by reacting imidazole with the corresponding alkyl halide or an acid chloride in the presence of base, or they may also readily be synthesized by selecting the raw materials for completing a ring.

SYNTHESIS EXAMPLE 1

Synthesis of Exemplified Compound 1

A solution was prepared by dissolving 15 g of 4-aminosalicylic acid and 11 g of phenylenediamine in 150 ml of dioxane, and 20 g of N,N'-dicyclohexylcarbodiimide was dropped into the solution so as to react them for 4 hours at room temperature. Urea and, then, the solvent were removed from the solution. The resulting solution was heated for 1 hour at 120° C. and, then, refined. Yield was 10 g. The total amount thereof was dissolved in 100 ml of acetonitrile and 7 g of benzoyl chloride was added. The resulting solution was refluxed for 3 hours, and the resulting reacted solution was cooled down, so that 13 g of the objective crystals were obtained, The structure of the crystals were confirmed with an NMR and an FD mass-spectrometer.

SYNTHESIS EXAMPLE 2

Synthesis of Exemplified Compound 6 p-nitrobenzamidine of 10.25 g was suspended in 50 ml of dimethyl formamide and 3.11 g of bromacetophenone was then added to the suspension. The suspension became exothermic and the color thereof was changed into reddish-brown. After the reddish-brown solution was cooled down, water was added. The resulting solid matters deposited were filtrated.

Yield: 2.27 g

The structure of the solid matters were confirmed with an NMR and an FD mass-spectrometer.

Melting point: 231° C.

SYNTHESIS EXAMPLE 3

Synthesis of Exemplified Compound 7 o-aminoacetophenone of 6.75 g was dissolved in 60 ml of acetonitrile. Pyridine of 5 ml was added. Benzoyl chloride of benzoyl chloride was dropped in while stirring. After $ hours, the solvents were distilled off under reduced pressure. An extraction was carried out by adding water and ethyl acetate. An organic layer was dehydrated with anhydrous magnesium sulfate and then the solvents were distilled off.

A crystallization deposition was carried out with alcohol. White crystals of o-benzamidobromacetophenone were thereby obtained. Yield: 9.6 g In place of the bromacetophenone used in Example 2, 4.97 g of o-benzamidobromacetophenone prepared as mentioned above was so used as to be reacted in the same manner as in Example 2, and a recrystallization was carried out with alcohol. Yield: 3.65 g The structure of the resulting matter was confirmed with an NMR and a FD mass-spectrometer.

Melting point: Not lower than 250° C.

The compounds of the invention may be used as a non-linear optical device, when the compounds are in various forms including, for example, a single crystalline form, a powder form, a liquid form, thin films such as Langmuir-Blodgett film, a vacuum-evaporated film and so forth, the other forms in which the compound is blended in polymers or liquid-crystal molecules, and so forth. The compounds of the invention may also be made pendent to a polymer or used as a clathrate compound or an addition product.

When a non-linear optical device is applied to the non-linear optical material of the invention, such device may be in any publicly known waveguide form. As is described in Japanese Patent O.P.I. Publication No. 63-77035/1988, these forms include, for example, a fibre form, a tabular form, and a form in which a single crystal is surrounded by a cladding material.

The non-linear optical devices of the invention may be frequency conversion and modulation of laser beams, i.e., generation of the higher harmonic wave, parametric amplification, intensity modulation, optical switching, and so forth.

EXAMPLES

Now, the examples will be described below. It is, however, to be understood that the embodiments of the invention shall not be limited thereto.

EXAMPLE-1

The compounds of the invention were evaluated for judging the SHG effect, by the well-known powder method. (Refer to S.K. Kurtz and T.T. Perry; J. Appl. Phys., 39, 3798, 1968.)

The following light source was used. A Q-switched Nd:YAG laser (the wavelength is 1064 nm) Model YG660A manufactured by Quantel International, Inc., U.S.A., having a beam diameter of 2 mm, a repetition rate of 10 pps, a pulse width of 10 ns, and a pulse energy of 20 mJ. A powdered sample filled in a glass-cell was exposed to the laser beam. The product SHG light, 532-nm green light, was spectrally separated by means of a filter and a monochrometer, and intensity of which was detected by means of a photomultiplier tube, so as to obtain the intensity of SHG of each sample relative to that of urea which is regarded as a value of 1.

The results thereof are also shown in Table 1, below.

TABLE 1

| Compound | SHG Intensity | Remark |
|---|---|---|
| Urea | 1 for Standard | Comparative |
| m-nitroaniline | 6 | Comparative |
| Example 1 | 7 | Invention |
| Example 4 | 10 | Invention |
| Example 6 | 15 | Invention |
| Example 7 | 16 | Invention |
| Example 15 | 8 | Invention |

As is apparent from Table 1, it can be found that the compounds of the invention are excellent non-linear optical materials high in SHG intensity.

EXAMPLE 2

The same compounds of the invention as those used in Example 1 were crystallized inside a hollow glass fibre so as to make the non-linear optical devices. When the Nd:YAG laser beam was coupled into these devices from the end-face of the fibre.

What is claimed is:

1. A non-linear optical device in wave-guide form comprising a compound selected from the group consisting of

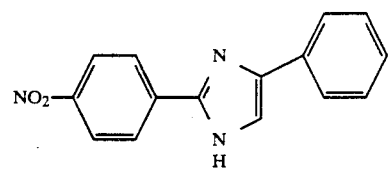

and

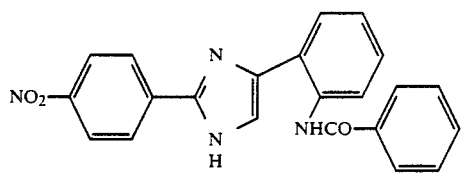

2. The device of claim 1 wherein said compound has a planar crystal form.

3. The device of claim 1, wherein said device has a fibre form.

4. The device of claim 1, wherein said device has a form in which a single crystal of said compound is surrounded by a cladding material.

* * * * *